United States Patent
Greene et al.

(10) Patent No.: US 12,304,948 B2
(45) Date of Patent: *May 20, 2025

(54) FULLY HUMANIZED ANTI-PLATELET FACTOR 4 ANTIBODIES THAT TREAT HEPARIN-INDUCED THROMBOCYTOPENIA

(71) Applicant: THE TRUSTEES OF THE UNIVERSITY OF PENNSYLVANIA, Philadelphia, PA (US)

(72) Inventors: Mark I. Greene, Penn Valley, PA (US); Zheng Cai, Wynnewood, PA (US); Zhiqiang Zhu, Philadelphia, PA (US); Douglas B. Cines, Wynnewood, PA (US)

(73) Assignee: THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 9 days.

This patent is subject to a terminal disclaimer.

(21) Appl. No.: 18/071,057

(22) Filed: Nov. 29, 2022

(65) Prior Publication Data

US 2023/0265180 A1    Aug. 24, 2023

Related U.S. Application Data

(63) Continuation of application No. 16/611,613, filed as application No. PCT/US2018/032213 on May 11, 2018, now Pat. No. 11,524,999.

(60) Provisional application No. 62/505,303, filed on May 12, 2017.

(51) Int. Cl.
| C07K 16/24 | (2006.01) |
| A61K 31/702 | (2006.01) |
| A61K 31/727 | (2006.01) |
| C12N 15/85 | (2006.01) |
| A61K 38/00 | (2006.01) |
| A61K 39/395 | (2006.01) |

(52) U.S. Cl.
CPC ............ *C07K 16/24* (2013.01); *A61K 31/702* (2013.01); *A61K 31/727* (2013.01); *C12N 15/85* (2013.01); *A61K 38/00* (2013.01); *A61K 39/39533* (2013.01); *C07K 2317/24* (2013.01); *C07K 2317/31* (2013.01); *C07K 2317/54* (2013.01); *C07K 2317/55* (2013.01); *C07K 2317/565* (2013.01); *C07K 2317/569* (2013.01); *C07K 2317/622* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| 4,816,567 | A | 3/1989 | Cabilly et al. |
| 5,225,539 | A | 7/1993 | Winter |
| 5,585,089 | A | 12/1996 | Queen et al. |
| 5,693,761 | A | 12/1997 | Queen et al. |
| 5,693,762 | A | 12/1997 | Queen et al. |
| 5,859,205 | A | 1/1999 | Adair et al. |
| 5,939,598 | A | 8/1999 | Kucherlapati et al. |
| 6,964,854 | B1 | 11/2005 | Arepally et al. |
| 7,728,115 | B2 | 6/2010 | Arepally et al. |
| 10,371,705 | B2 | 8/2019 | Greene et al. |
| 11,524,999 | B2 * | 12/2022 | Greene ................. C07K 16/22 |
| 2018/0024140 | A1 | 1/2018 | Greene et al. |

FOREIGN PATENT DOCUMENTS

WO    2016/073747 A1    5/2016

OTHER PUBLICATIONS

Kohler et al., "Continuous cultures of fused cells secreting antibody of predefined specificity", Nature, 1975, vol. 256, No. 5517, pp. 495-497.
Kozbor et al., "The production of monoclonal antibodies from human lymphocytes", Immunology Today, 1983, vol. 4, No. 3, pp. 72-79.
Marks et al., "By-passing immunization: Human antibodies from V-gene libraries displayed on phage", J. Mol. Biol., 1991, vol. 222, No. 3, pp. 581-597.
Chothia et al., "Canonical Structures for the Hypervariable Regions of Immunoglobulins", J. Mol. Biol., 1987, vol. 196, pp. 901-917.
Clackson et al., "Making antibody fragments using phage display libraries", Nature, Aug. 1991, vol. 352, pp. 624-628.
Cole et al., In Monoclonal Antibodies and Cancer Therapy, Alan R. Liss, Inc., 1985, pp. 77-96.
Jones et al., "Replacing the complementarity-determining regions in a human antibody with those from a mouse", Nature, 1986, vol. 321, pp. 522-525.
McMahon et al., "Inappropriate documentation of heparin allergy in the medical record because of misdiagnosis of heparin-induced thrombocytopenia: frequency and consequences", J. Thrombosis and Haemostasis, 2016, vol. 15, No. 2, pp. 370-374.
Presta, "Antibody engineering", Curr. Opin. Struct. Biol., 1992, vol. 2, pp. 593-596.

(Continued)

*Primary Examiner* — Marianne P Allen
(74) *Attorney, Agent, or Firm* — BakerHostetler (57) ABSTRACT

Provided herein are isolated antibodies or antibody fragments thereof that immunospecifically bind to platelet factor 4 (PF4). In some embodiments the isolated antibodies or antigen-binding fragments thereof comprise a light chain CDR and framework region comprising SEQ ID NO: 4 and a heavy chain CDR and framework region comprising SEQ ID NO: 10. Also provided herein are methods for treating heparin-induced thrombocytopenia (HIT) and methods for reducing the likelihood that subject will become afflicted with HIT. Further disclosed are uses of the isolated antibodies or antibody fragments in the treatment of HIT or the manufacture of compositions for the treatment of HIT.

18 Claims, 3 Drawing Sheets

Specification includes a Sequence Listing.

(56) References Cited

OTHER PUBLICATIONS

Riechmann et al., "Reshaping human antibodies for therapy", Nature, 1988, vol. 332, pp. 323-327.
Udeh et al., "Heparin-induced thrombocytopenia: a clinical and economic review", OA Anaesthetics, 2013, 1(1):3, 9 pages.

\* cited by examiner

```
                              SEQUENCE LISTING

Sequence total quantity: 12
SEQ ID NO: 1            moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 1
SASQGINNYL S                                                                11

SEQ ID NO: 2            moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 2
YTSSLHS                                                                     7

SEQ ID NO: 3            moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 3
QQFSKLPYT                                                                   9

SEQ ID NO: 4            moltype = AA  length = 74
FEATURE                 Location/Qualifiers
REGION                  1..74
                        note = Description of Artificial Sequence: Synthetic
                         polypeptide
source                  1..74
                        mol_type = protein
                        organism = synthetic construct
SEQUENCE: 4
SASQGINNYL SWYRQKPGKA PKLLIYYTSS LHSGVPSRFS GSGSGTDFTL TISSLQPEDF    60
ATYFCQQFSK LPYT                                                     74

SEQ ID NO: 5            moltype = AA  length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 5
DIQMTQSPSS LSASVGDRVT ISCSASQGIN NYLSWYRQKP GKAPKLLIYY TSSLHSGVPS    60
RFSGSGSGTD FTLTISSLQP EDFATYFCQQ FSKLPYTFGG GTKVEIK                  107

SEQ ID NO: 6            moltype = AA  length = 214
FEATURE                 Location/Qualifiers
REGION                  1..214
                        note = Description of Artificial Sequence: Synthetic
                         polypeptide
source                  1..214
                        mol_type = protein
                        organism = synthetic construct
SEQUENCE: 6
DIQMTQSPSS LSASVGDRVT ISCSASQGIN NYLSWYRQKP GKAPKLLIYY TSSLHSGVPS    60
RFSGSGSGTD FTLTISSLQP EDFATYFCQQ FSKLPYTFGG GTKVEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                                214

SEQ ID NO: 7            moltype = AA  length = 10
FEATURE                 Location/Qualifiers
REGION                  1..10
```

```
                        note = Description of Artificial Sequence: Synthetic peptide
source                  1..10
                        mol_type = protein
                        organism = synthetic construct
SEQUENCE: 7
GFAFSRYDMS                                                                       10

SEQ ID NO: 8            moltype = AA   length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 8
TITSGDNYTY YPDSVKG                                                               17

SEQ ID NO: 9            moltype = AA   length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 9
QGLLYYAMDY                                                                       10

SEQ ID NO: 10           moltype = AA   length = 83
FEATURE                 Location/Qualifiers
REGION                  1..83
                        note = Description of Artificial Sequence: Synthetic
                         polypeptide
source                  1..83
                        mol_type = protein
                        organism = synthetic construct
SEQUENCE: 10
GFAFSRYDMS WVRQAPGKGL EWVATITSGD NYTYYPDSVK GRFTISRDNS KNTLYLQMNS                 60
LRAEDTAVYY CTRQGLLYYA MDY                                                        83

SEQ ID NO: 11           moltype = AA   length = 119
FEATURE                 Location/Qualifiers
REGION                  1..119
                        note = Description of Artificial Sequence: Synthetic
                         polypeptide
source                  1..119
                        mol_type = protein
                        organism = synthetic construct
SEQUENCE: 11
EVQLVESGGG LVQPGGSLRL SCAASGFAFS RYDMSWVRQA PGKGLEWVAT ITSGDNYTYY                 60
PDSVKGRFTI SRDNSKNTLY LQMNSLRAED TAVYYCTRQG LLYYAMDYWG QGTLVTVSS                  119

SEQ ID NO: 12           moltype = AA   length = 446
FEATURE                 Location/Qualifiers
REGION                  1..446
                        note = Description of Artificial Sequence: Synthetic
                         polypeptide
source                  1..446
                        mol_type = protein
                        organism = synthetic construct
SEQUENCE: 12
EVQLVESGGG LVQPGGSLRL SCAASGFAFS RYDMSWVRQA PGKGLEWVAT ITSGDNYTYY                 60
PDSVKGRFTI SRDNSKNTLY LQMNSLRAED TAVYYCTRQG LLYYAMDYWG QGTLVTVSSA                 120
STKGPSVFPL APSSKSTSGG TAALGCLVKD YFPEPVTVSW NSGALTSGVH TFPAVLQSSG                 180
LYSLSSVVTV PSSSLGTQTY ICNVNHKPSN TKVDKKVEPK YGPPCPSCPA PEFLGGPSVF                 240
LFPPKPKDTL MISRTPEVTC VVVDVSQEDP EVQFNWYVDG VEVHNAKTKP REEQFNSTYR                 300
VVSVLTVLHQ DWLNGKEYKC KVSNKGLPSS IEKTISKAKG QPREPQVYTL PPSPEEMTKN                 360
QVSLTCLVKG FYPSDIAVEW ESNGQPENNY KTTPPVLDSD GSFFLYSRLT VDKSRWQEGN                 420
VFSCSVMHEA LHNHYTQKSL SLSLGK                                                     446
```

FULLY HUMANIZED ANTI-PLATELET FACTOR 4 ANTIBODIES THAT TREAT HEPARIN-INDUCED THROMBOCYTOPENIA

CROSS REFERENCE TO RELATED APPLICATIONS

This application is a continuation of U.S. patent application Ser. No. 16/611,613, filed Nov. 7, 2019, which is the National Stage Application of International Patent Application No. PCT/US2018/032213, filed May 11, 2018, which claims the benefit of U.S. Provisional Patent Application No. 62/505,303, filed May 12, 2017, the entirety of each of which are incorporated by reference.

GOVERNMENT RIGHTS

This invention was made with government support under HL110860 awarded by the National Institutes of Health. The government has certain rights in the invention.

SEQUENCE LISTING

The instant application contains a sequence listing which has been submitted electronically in XML format and is hereby incorporated by reference in its entirety. The XML copy, created on May 8, 2023, is named 103241006892_Sequence Listing.xml and is 17,498 bytes in size.

FIELD OF THE INVENTION

Provided herein are isolated antibodies that immunospecifically bind to platelet factor 4 (PF4) and methods of using the same.

BACKGROUND OF THE INVENTION

Heparin is a commonly used anti-coagulant. It prevents the formation of new blood clots and stops the enlargement of existing clots. Heparin can sometimes bind to and form a complex with platelet factor 4 (PF4), a protein made by platelets (cell fragments that aggregate to form blood clots). Roughly 12 million patients are exposed to heparin annually (Eke, Sankar, Heparin-Induced Thrombocytopenia, Medscape, ed. Emmanuel Besa, 2014, available at emedicine.medscape.com/article/1357846-overview) and a subset of these patients will develop heparin-induced thrombocytopenia (HIT), a life-threatening complication where patients make antibodies that bind to the heparin/PF4 complex. These antibodies trigger the activation and aggregation of platelets, resulting in blood clots ("thrombosis") and the depletion of platelets ("thrombocytopenia").

HIT leads to longer hospital stays and increased morbidity and mortality, resulting in significant additional treatment costs. For example, among US medical patients who developed HIT, hospital costs were reported to be higher by an average of ~$41,000 compared to patients without HIT (Udeh et al. (2013) Heparin-induced thrombocytopenia: a clinical and economic review. *OA Anaesthetics* 1(1):3). Healthcare institutions and insurance companies incur additional costs when HIT is falsely diagnosed, as these misdiagnosed patients are given unnecessary anti-coagulants (which can be more expensive and which can increase the risk of bleeding, leading to subsequent complications) (C. M. McMahon, et al. (2017) Inappropriate documentation of heparin allergy in the medical record because of misdiagnosis of heparin-induced thrombocytopenia: frequency and consequences, J. Thrombosis and Haemostasis, Vol. 15 (2), p. 370-374).

Typically, management of HIT consists of stopping the heparin and using an alternative anti-coagulant. These alternative drugs are often inhibitors of thrombin or inhibitors of the enzyme factor Xa.

SUMMARY OF THE INVENTION

Disclosed herein are isolated antibodies, or antigen-binding fragments thereof, that immunospecifically bind to platelet factor 4 (PF4), the antibody or antigen-binding fragment thereof comprising a light chain CDR and framework region comprising SEQ ID NO: 4 and a heavy chain CDR and framework region comprising SEQ ID NO: 10.

Further disclosed herein are isolated antibodies, or antigen-binding fragments thereof, that immunospecifically bind to platelet factor 4 (PF4), wherein the isolated antibodies or antigen-binding fragments thereof have a light chain variable domain comprising an amino acid sequence that is at least 95% identical to the amino acid sequence of SEQ ID NO: 5 and a heavy chain variable domain comprising an amino acid sequence that is at least 95% identical to the amino acid sequence of SEQ ID NO: 11, wherein the variable occurs outside of the light chain and heavy chain CDRs.

Provided herein are isolated antibodies, or antigen-binding fragments thereof, that immunospecifically bind to platelet factor 4 (PF4), wherein the isolated antibodies or antigen-binding fragments thereof have a light chain variable domain comprising the amino acid sequence of SEQ ID NO: 5 and a heavy chain variable domain comprising the amino acid sequence of SEQ ID NO: 11. In some embodiments, the light chain variable domain has the amino acid sequence of SEQ ID NO: 5 and the heavy chain variable domain has the amino acid sequence of SEQ ID NO: 11.

Also provided herein are isolated antibodies, or antigen-binding fragments thereof, that immunospecifically bind to platelet factor 4 (PF4), wherein the isolated antibodies or antigen-binding fragments thereof have a light chain comprising an amino acid sequence that is at least 95% identical to the amino acid sequence of SEQ ID NO: 6 and a heavy chain comprising an amino acid sequence that is at least 95% identical to the amino acid sequence of SEQ ID NO: 12, wherein the variable occurs outside of the light chain and heavy chain CDRs.

Also disclosed herein are isolated antibodies, or antigen-binding fragments thereof, that immunospecifically bind to platelet factor 4 (PF4), wherein the isolated antibodies or antigen-binding fragments thereof have a light chain comprising the amino acid sequence of SEQ ID NO: 6 and a heavy chain comprising the amino acid sequence of SEQ ID NO: 12. In some embodiments, the light chain has the amino acid sequence of SEQ ID NO: 6 and the heavy chain has the amino acid sequence of SEQ ID NO: 12.

Further disclosed herein are isolated antibodies, or antigen-binding fragments thereof, that immunospecifically bind to platelet factor 4 (PF4), wherein the isolated antibodies or antigen-binding fragments thereof are humanized.

Also provided herein are isolated antibodies, or antigen-binding fragments thereof, that immunospecifically bind to platelet factor 4 (PF4), wherein the antibody isotype is IgG. In some embodiments, the antigen-binding fragments are a Fv, Fab, Fab', Fab'-SH or F(ab')2. In some embodiments, the antibodies are a single chain antibody, a diabody, or a multispecific antibody formed from more than one antigen-binding fragment Provided herein are isolated antibodies, or antigen-binding fragments thereof, that immunospecifically bind to platelet factor 4 (PF4), wherein the isolated antibodies or antigen-binding fragments thereof have an equilibrium dissociation constant (KD) of less than about 5 nM with platelet factor 4 (PF4).

Also disclosed herein are isolated antibodies, or antigen-binding fragments thereof, that immunospecifically bind to platelet factor 4 (PF4), which can bind at least a portion of the same epitope to which RTO binds so as to reduce platelet factor 4 (PF4) oligomerization. In some embodiments are provided, the isolated antibodies, or antigen-binding fragments thereof, that immunospecifically bind to platelet factor 4 (PF4), wherein the epitope overlaps with a portion of the same epitope to which KKO binds. In some embodiments the isolated antibodies, or antigen-binding fragments thereof, that immunospecifically bind to platelet factor 4 (PF4), can bind to the same epitope as the epitope to which RTO binds. In some embodiments, the isolated antibodies, or antigen-binding fragments thereof, that immunospecifically bind to platelet factor 4 (PF4), can reduce PF4 oligomerization. In some embodiments, the oligomerization is dimerization or tetramerization. In some embodiments, the isolated antibodies, or antigen-binding fragments thereof, that immunospecifically bind to platelet factor 4 (PF4), can reduce the binding of KKO to PF4. In some embodiments, the isolated antibodies, or antigen-binding fragments thereof, that immunospecifically bind to platelet factor 4 (PF4), can bind between the PF4 AB dimer interface.

Also provided are pharmaceutical compositions comprising the isolated antibodies or antigen-binding fragments thereof described herein, and vectors encoding the isolated antibodies or antigen-binding fragments thereof described herein.

Recombinant cells expressing the isolated antibodies or antigen-binding fragments thereof described herein. The recombinant cells can be a eukaryotic cell, a yeast cell, a plant cell or a bacterium. In some embodiments, the eukaryotic cells are a 293T cell or a Chinese Hamster Ovary (CHO) cell.

Methods of treating a subject having heparin-induced thrombocytopenia (HIT), the methods comprising administering to the subject a therapeutically effective amount of any of the disclosed isolated antibodies or antigen-binding fragments thereof so as to treat HIT are also provided. In some embodiments, administering to the subject a therapeutically effective amount of the isolated antibody or antigen-binding fragment treats HIT by reducing platelet factor 4 (PF4) oligomerization.

Also disclosed herein are methods for reducing the likelihood that a subject receiving the administration of heparin or a heparin-mimic will become afflicted with HIT, the methods comprising administering to the subject a therapeutically effective amount of any of the disclosed isolated antibodies or antigen-binding fragments thereof. In some embodiments, administering to the subject a therapeutically effective amount of the isolated antibody or antigen-binding fragment reduces the likelihood that a subject receiving the administration of heparin or a heparin-mimic will become afflicted with HIT by reducing platelet factor 4 (PF4) oligomerization. In some embodiments, the isolated antibody or antigen-binding fragment thereof is administered before, after or concurrently with heparin. In some embodiments, the heparin is a heparin fragment, low-molecular-weight heparin or unfractionated heparin. The isolated antibodies or antigen-binding fragments thereof can be administered before, after or concurrently with a heparin mimic. In some embodiments, the heparin mimic is fondaparinux.

Also disclosed herein are uses of an effective amount of any of the disclosed isolated antibodies or antigen-binding fragments thereof in the treatment of heparin-induced thrombocytopenia (HIT).

Provided herein are uses of any of the disclosed isolated antibodies or antigen-binding fragments thereof in the manufacture of a composition for the treatment of heparin-induced thrombocytopenia (HIT).

BRIEF DESCRIPTION OF THE DRAWINGS

The summary, as well as the following detailed description, is further understood when read in conjunction with the appended drawings. For the purpose of illustrating the disclosed compositions and methods there are shown in the drawings exemplary embodiments of the isolated antibodies and methods; however, the isolated antibodies and methods are not limited to the specific embodiments disclosed. In the drawings:

FIG. 1 illustrates binding of huRTO (with human IgG4 Fc) to immobilized human PF4 confirmed by ELISA test using goat anti-mouse and anti-human IgG Fc antibodies. Binding of huRTO to PF4 is independent of heparin.

FIG. 2A-FIG. 2B illustrate mean fluorescence intensity of P selection expression (FIG. 2A) and Annexin binding (FIG. 2B) on platelets by flow cytometry. mRTO or huRTO was added at indicated concentrations to PF4 before adding whole blood, and where the samples were then stimulated with 10 μg/ml of KKO for 30 min and platelet activation was monitored.

FIG. 3 illustrates the effect of huRTO on KKO induced thrombosis in a laser microvascular injury model. Antibodies (TRA (isotype control), RTO and huRTO) were injected intravenously. Each dot denotes the percent change in thrombus size based on binding of fluorescently labelled platelets in mice receiving either huRTO, RTO or the TRA followed by KKO.

DETAILED DESCRIPTION OF ILLUSTRATIVE EMBODIMENTS

The disclosed isolated antibodies and methods may be understood more readily by reference to the following detailed description taken in connection with the accompanying figures, which form a part of this disclosure. It is to be understood that the disclosed isolated antibodies and methods are not limited to the specific antibodies and methods described and/or shown herein, and that the terminology used herein is for the purpose of describing particular embodiments by way of example only and is not intended to be limiting of the claimed antibodies and methods.

Unless specifically stated otherwise, any description as to a possible mechanism or mode of action or reason for improvement is meant to be illustrative only, and the disclosed antibodies and methods are not to be constrained by the correctness or incorrectness of any such suggested mechanism or mode of action or reason for improvement.

Throughout this text, the descriptions refer to isolated antibodies and methods of using said antibodies. Where the disclosure describes or claims a feature or embodiment associated with an antibody, such a feature or embodiment is equally applicable to the methods of using said antibody. Likewise, where the disclosure describes or claims a feature or embodiment associated with a method of using an antibody, such a feature or embodiment is equally applicable to the antibody.

When a range of values is expressed, another embodiment includes from the one particular value and/or to the other particular value. Further, reference to values stated in ranges include each and every value within that range. All ranges are inclusive and combinable. When values are expressed as approximations, by use of the antecedent "about," it will be understood that the particular value forms another embodiment. Reference to a particular numerical value includes at least that particular value, unless the context clearly dictates otherwise.

It is to be appreciated that certain features of the disclosed isolated antibodies and methods which are, for clarity, described herein in the context of separate embodiments, may also be provided in combination in a single embodiment. Conversely, various features of the disclosed isolated antibodies and methods that are, for brevity, described in the context of a single embodiment, may also be provided separately or in any subcombination.

Various terms relating to aspects of the description are used throughout the specification and claims. Such terms are to be given their ordinary meaning in the art unless otherwise indicated. Other specifically defined terms are to be construed in a manner consistent with the definitions provided herein.

Abbreviations—PF4 (platelet factor 4), HC (heavy chain), LC (light chain), VL (variable light), and VH (variable heavy).

Definitions

As used herein, the singular forms "a," "an," and "the" include the plural.

The term "about" when used in reference to numerical ranges, cutoffs, or specific values is used to indicate that the recited values may vary by up to as much as 10% from the listed value. Thus, the term "about" is used to encompass variations of ±10% or less, variations of ±5% or less, variations of ±1% or less, variations of ±0.5% or less, or variations of ±0.1% or less from the specified value.

The term "comprising" is intended to include examples encompassed by the terms "consisting essentially of" and "consisting of"; similarly, the term "consisting essentially of" is intended to include examples encompassed by the term "consisting of."

The term "PF4" (SwissProt P02776) refers to the human platelet factor 4, a member of the CXC chemokine family that is made by platelets and is released in the form of monomers, dimers or tetramers. Each monomer contains three-stranded antiparallel β-sheets upon which an aperiodic N-terminal domain and an amphipathic C-terminal α-helix are folded.

"Isolated" means a biological component (such as an antibody) has been substantially separated, produced apart from, or purified away from other biological components of the organism in which the component naturally occurs, i.e., other chromosomal and extrachromosomal DNA and RNA and proteins. Antibodies that have been "isolated" include antibodies purified by standard purification methods. "Isolated antibodies" can be part of a composition and still be isolated if such composition is not part of the native environment of the antibody. The term also embraces antibodies prepared by recombinant expression in a host cell as well as chemically synthesized antibodies. An "isolated antibody or antigen-binding fragment thereof," as used herein, is intended to refer to an antibody or antigen-binding fragment thereof which is substantially free of other antibodies or antigen-binding fragments having different antigenic specificities (for instance, an isolated antibody that specifically binds to PF4 is substantially free of antibodies that specifically bind antigens other than PF4). An isolated antibody that specifically binds to an epitope, isoform, or variant of PF4 may, however, have cross-reactivity to other related antigens, for instance from other species (such as PF4 species homologs).

"Antibody" refers to all isotypes of immunoglobulins (IgG, IgA, IgE, IgM, IgD, and IgY) including various monomeric, polymeric and chimeric forms, unless otherwise specified. Specifically encompassed by the term "antibody" are polyclonal antibodies, monoclonal antibodies (mAbs), and antibody-like polypeptides.

"Antigen-binding fragments" comprise a portion of a full length antibody, generally the antigen binding or variable region thereof. Examples of antigen-binding fragments include but are not limited to Fv, Fab, Fab', Fab'-SH, F(ab')2; diabodies; linear antibodies; single-chain antibody molecules (e.g., scFv); and multispecific antibodies formed from antigen-binding fragments. Various techniques have been developed for the production of antigen-binding fragments, including proteolytic digestion of antibodies and recombinant production in host cells; however, other techniques for the production of antigen-binding fragments will be apparent to the skilled practitioner. In some embodiments, the antigen-binding fragment of choice is a single chain Fv fragment (scFv). "Single-chain Fv" or "scFv" antigen-binding fragments comprise the VH and VL domains of antibody, wherein these domains are present in a single polypeptide chain. Generally, the Fv polypeptide further comprises a polypeptide linker between the VH and VL domains which enables the scFv to form the desired structure for antigen binding. For a review of scFv and other antigen-binding fragments, see James D. Marks, Antibody Engineering, Chapter 2, Oxford University Press (1995) (Carl K. Borrebaeck, Ed.).

"Immunospecifically" when used in the context of antibodies, or antigen-binding fragments, refers to binding via domains encoded by immunoglobulin genes or fragments of immunoglobulin genes to one or more epitopes of a protein of interest, without preferentially binding other molecules in a sample containing a mixed population of molecules. Typically, an antibody binds to a cognate antigen with a Kd of less than about $1 \times 10^{-8}$ M, as measured by a surface plasmon resonance assay or a cell binding assay. Thus, antibodies or antigen-binding fragments thereof that immunospecifically bind PF4 refer to an antibody or antigen-binding fragment thereof that binds PF4 without preferentially binding other molecules in a sample containing a mixed population of molecules. The term "anti-PF4" and "immunospecifically binds PF4" are used interchangeably.

The term "epitope" refers to a portion of a molecule (the antigen) can be bound by an antibody, at one or more of the antibody's antigen binding regions. Epitopes usually consist of specific three-dimensional structural characteristics, as well as specific charge characteristics.

As used herein, "monoclonal antibody" means an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations that typically include different antibodies directed against different determinants, each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present disclosure may be made by the hybridoma method first described by Kohler and Milstein, Nature 256:495-97 (1975), or may be made by recombinant DNA methods (see, e.g., U.S. Pat. No. 4,816,567). The monoclonal antibodies may also be isolated from phage display libraries using the techniques described, for example, in Clackson et al., Nature 352:624-28 (1991) and Marks et al., J. Mol. Biol. 222(3): 581-97 (1991).

The term "hybridoma" or "hybridoma cell line" refers to a cell line derived by cell fusion, or somatic cell hybridization, between a normal lymphocyte and an immortalized lymphocyte tumor line. In particular, B cell hybridomas are created by fusion of normal B cells of defined antigen specificity with a myeloma cell line, to yield immortal cell lines that produce monoclonal antibodies. In general, techniques for producing human B cell hybridomas, are well known in the art (Kozbor et al., Immunol. Today 4:72 (1983); Cole et al., in Monoclonal Antibodies and Cancer Therapy, Alan R. Liss, Inc. 77-96 (1985)).

The term "humanized antibodies" means antibodies that contain minimal sequence derived from non-human immunoglobulin sequences. For the most part, humanized antibodies are human immunoglobulins (recipient antibody) in which residues from a hyper variable region of the recipient are replaced by residues from a hypervariable region of a non-human species (donor antibody) such as mouse, rat, rabbit or nonhuman primate having the desired specificity, affinity, and capacity. See, for example, U.S. Pat. Nos. 5,225,539; 5,585,089; 5,693,761; 5,693,762; 5,859,205, each herein incorporated by reference. In some instances, framework residues of the human immunoglobulin are replaced by corresponding non-human residues (see, for example, U.S. Pat. Nos. 5,585,089; 5,693,761; 5,693,762, each herein incorporated by reference). Furthermore, humanized antibodies may comprise residues that are not found in the recipient antibody or in the donor antibody. These modifications are made to further refine antibody performance (e.g., to obtain desired affinity). In general, the humanized antibody will comprise substantially all of at least one, and typically two, variable domains, in which all or substantially all of the hypervariable regions correspond to those of a non-human immunoglobulin and all or substantially all of the framework regions are those of a human immunoglobulin sequence. The humanized antibody optionally also will comprise at least a portion of an immunoglobulin constant region (Fc), typically that of a human immunoglobulin. For further details see Jones et al., Nature 331:522-25 (1986); Riechmann et al., Nature 332:323-27 (1988); and Presta, Curro Opin. Struct. Biol. 2:593-96 (1992), each of which is incorporated herein by reference.

An immunoglobulin light or heavy chain variable region consists of a "framework" region interrupted by three hypervariable regions. Thus, the term "hypervariable region" refers to the amino acid residues of an antibody which are responsible for antigen binding. The hypervariable region comprises amino acid residues from a "Complementarity Determining Region" or "CDR" and/or those residues from a "hypervariable loop" in the heavy chain variable domain; Chothia and Lesk, 1987, J. Mol. Biol. 196: 901-917).

"Framework Region" or "FR" residues are those variable domain residues other than the hypervariable region residues as herein defined. The sequences of the framework regions of different light or heavy chains are relatively conserved within a species. Thus, a "human framework region" is a framework region that is substantially identical (about 85% or more, usually 90-95% or more, such as 100%) to the framework region of a naturally occurring human immunoglobulin. The framework region of an antibody, that is the combined framework regions of the constituent light and heavy chains, serves to position and align the CDR's. The CDR's are primarily responsible for binding to an epitope of an antigen.

As used herein, the term "CDR and framework region" includes CDR1, CDR2, and CDR3 has well as the intervening framework regions.

Antibodies, as used herein, also include antibodies produced in a non-human mammalian host, more particularly a transgenic mouse, characterized by inactivated endogenous immunoglobulin (Ig) loci. In such transgenic animals, competent endogenous genes for the expression of light and heavy subunits of host immunoglobulins are rendered non-functional and substituted with the analogous human immunoglobulin loci. These transgenic animals produce human antibodies in the substantial absence of light or heavy host immunoglobulin subunits. See, for example, U.S. Pat. No. 5,939,598, the entire contents of which are incorporated herein by reference.

Those skilled in the art will be aware of how to produce antibody molecules. For example, polyclonal antisera or monoclonal antibodies can be made using standard methods. A mammal, (e.g., a mouse, hamster, or rabbit) can be immunized with an immunogenic form of the protein which elicits an antibody response in the mammal. For instance, a mammal can be immunized with irradiated cells that were transfected with a nucleic acid encoding the protein such that high levels of the protein were expressed on the cell surface. The progress of immunization can be monitored by detection of antibody titers in plasma or serum. Standard ELISA or other immunoassay can be used with the immunogen as antigen to assess the levels of antibodies. Following immunization, antisera can be obtained, and, if desired IgG molecules corresponding to the polyclonal antibodies may be isolated from the sera.

To produce monoclonal antibodies, antibody producing cells (lymphocytes) can be harvested from an immunized animal and fused with myeloma cells by standard somatic cell fusion procedures thus immortalizing these cells and yielding hybridoma cells. Such techniques are well known in the art. Hybridoma cells can be screened immunochemically for production of antibodies which are specifically reactive with the oligopeptide, and monoclonal antibodies isolated.

"Subject" refers to human and non-human animals, including all vertebrates, e.g., mammals and non-mammals, such as non-human primates, mice, rabbits, sheep, dogs, cats, horses, cows, chickens, amphibians, and reptiles. In many embodiments of the described methods, the subject is a human.

"Treating" or "treatment" refer to any success or indicia of success in the attenuation or amelioration of an injury, pathology, or condition, including any objective or subjective parameter such as abatement, remission, diminishing of symptoms or making the condition more tolerable to the patient, slowing in the rate of degeneration or decline, making the final point of degeneration less debilitating, improving a subject's physical or mental well-being, or prolonging the length of survival. The treatment may be assessed by objective or subjective parameters, including the results of a physical examination, neurological examination, or psychiatric evaluations.

"Effective amount" and "therapeutically effective amount" are used interchangeably herein, and refer to an amount of a compound effective to achieve a particular biological or therapeutic result such as, but not limited to, biological or therapeutic results disclosed, described, or exemplified herein. A therapeutically effective amount of the compound may vary according to factors such as the disease state, age, sex, and weight of the subject, and the ability of the antibody or antigen-binding fragment thereof to elicit a desired response in the subject. In some embodiments, such results may include, but are not limited to, the treatment of heparin-induced thrombocytopenia (HIT), as determined by any means suitable in the art.

The term "KD" (M), as used herein, refers to the dissociation equilibrium constant of a particular antibody-antigen interaction.

Platelet Factor 4 Antibodies and Antigen-Binding Fragments

Disclosed herein are isolated antibodies, and antigen-binding fragments thereof, that immunospecifically bind to platelet factor 4 (PF4). The disclosed isolated antibodies and antigen-binding fragments thereof include those provided in Table 2.

Also disclosed herein are isolated antibodies, or antigen-binding fragments thereof, that immunospecifically bind to platelet factor 4 (PF4), the antibody or antigen-binding fragment thereof comprising a light chain CDR and framework region comprising SEQ ID NO: 4 and a heavy chain CDR and framework region comprising SEQ ID NO: 10.

Also disclosed herein are isolated antibodies, or antigen-binding fragments thereof, that immunospecifically bind to platelet factor 4 (PF4), wherein the isolated antibodies or antigen-binding fragments thereof have a light chain variable domain comprising an amino acid sequence that is at least 95% identical to the amino acid sequence of SEQ ID NO: 5 and a heavy chain variable domain comprising an amino acid sequence that is at least 95% identical to the amino acid sequence of SEQ ID NO: 11, wherein the variability occurs outside of the CDRs.

Also disclosed herein are isolated antibodies, or antigen-binding fragments thereof, that immunospecifically bind to platelet factor 4 (PF4), wherein the isolated antibodies or antigen-binding fragments thereof have a light chain variable domain comprising the amino acid sequence of SEQ ID NO: 5 and a heavy chain variable domain comprising the amino acid sequence of SEQ ID NO: 11. In some embodiments, the light chain variable domain has the amino acid sequence of SEQ ID NO: 5 and the heavy chain variable domain has the amino acid sequence of SEQ ID NO: 11.

Also disclosed herein are isolated antibodies, or antigen-binding fragments thereof, that immunospecifically bind to platelet factor 4 (PF4), wherein the isolated antibodies or antigen-binding fragments thereof have a light chain comprising an amino acid sequence that is at least 95% identical to the amino acid sequence of SEQ ID NO: 6 and a heavy chain comprising an amino acid sequence that is at least 95% identical to the amino acid sequence of SEQ ID NO: 12.

Also disclosed herein are isolated antibodies, or antigen-binding fragments thereof, that immunospecifically bind to platelet factor 4 (PF4), wherein the isolated antibodies or antigen-binding fragments thereof have a light chain comprising the amino acid sequence of SEQ ID NO: 6 and a heavy chain comprising the amino acid sequence of SEQ ID NO: 12. In some embodiments, the light chain has the amino acid sequence of SEQ ID NO: 6 and the heavy chain has the amino acid sequence of SEQ ID NO: 12.

The anti-PF4 antibodies and antigen-binding fragments thereof can be a human antibody or antigen-binding fragment thereof. In preferred embodiments, the isolated antibodies, or antigen-binding fragments thereof disclosed herein are humanized.

The disclosed anti-PF4 antibodies and antigen-binding fragments thereof include all isotypes (IgA, IgD, IgE, IgG and IgM) and synthetic multimers of the four-chain immunoglobulin (Ig) structure. In preferred embodiments, the antibody isotype is IgG.

The disclosed antibodies and antigen-binding fragments can also be derived from any of the Ig subclass. For example, the disclosed antibodies, or antigen-binding fragments thereof, can be derived from IgG1, IgG2, IgG3, and IgG4 isotypes. These subtypes share more than 95% homology in the amino acid sequences of the Fc regions but show major differences in the amino acid composition and structure of the hinge region. The Fc region mediates effector functions, such as antibody-dependent cellular cytotoxicity (ADCC) and complement-dependent cytotoxicity (CDC). In ADCC, the Fc region of an antibody binds to Fc receptors (FcgRs) on the surface of immune effector cells such as natural killers and macrophages, leading to the phagocytosis or lysis of the targeted cells. In CDC, the antibodies kill the targeted cells by triggering the complement cascade at the cell surface. The disclosed antibodies include antibodies with the described features of the variable domains in combination with any of the IgG isotypes, including modified versions in which the Fc sequence has been modified to effect different effector functions. In preferred embodiments, the isotype is IgG4, IgG1 or some combination of IgG4 and IgG1.

The antigen-binding fragments can be a Fv, Fab, Fab', Fab'-SH or F(ab')2. The antibodies can be single chain antibody, a diabody, or a multispecific antibody formed from more than one antigen-binding fragment.

The anti-PF4 antibodies and antigen-binding fragments thereof described herein can have binding affinities for PF4 that include an equilibrium dissociation constant (KD) of less than about 5 nM, 4 nM, 3 nM, 2 nM or 1 nM. The affinity of the described anti-PF4 antibodies or antigen-binding fragments thereof may be determined by a variety of methods known in the art, such as surface plasmon resonance or ELISA-based methods. Assays for measuring affinity by SPR include assays performed using a BIAcore 3000 machine, where the assay is performed at room temperature (e.g. at or near 25° C.), wherein human PF4 is captured on the BIAcore sensor chip 3000 RUs, followed by extensive wash and the collection of association and dissociation data at a flow rate of 20 µl/min. In preferred embodiments, the isolated antibodies or antigen-binding fragments thereof have an equilibrium dissociation constant (KD) of less than about 5 nM with platelet factor 4 (PF4).

The isolated antibodies, or antigen-binding fragments thereof, that immunospecifically bind to platelet factor 4 (PF4), can bind at least a portion of the same epitope as the epitope to which RTO binds so as to reduce platelet factor 4 (PF4) oligomerization. Provided herein are isolated antibodies, or antigen-binding fragments thereof, that immunospecifically bind to platelet factor 4 (PF4), wherein the epitope overlaps with a portion of the same epitope to which KKO binds. The isolated antibodies, or antigen-binding fragments thereof, that immunospecifically bind to platelet factor 4 (PF4), can bind to the same epitope as the epitope to which RTO binds. In some embodiments, the isolated antibodies, or antigen-binding fragments thereof, that immunospecifically bind to platelet factor 4 (PF4), can reduce PF4 oligomerization. In some embodiments, the oligomerization is dimerization or tetramerization. In some embodiments, the isolated antibodies, or antigen-binding fragments thereof, that immunospecifically bind to platelet factor 4 (PF4), can reduce the binding of KKO to PF4. In some embodiments, the isolated antibodies, or antigen-binding fragments thereof, that immunospecifically bind to platelet factor 4 (PF4), can bind between the PF4 AB dimer interface.

Further disclosed herein are pharmaceutical compositions comprising the isolated antibodies or antibody-binding fragments thereof described herein. In some embodiments, the pharmaceutical composition also comprises a pharmaceutically acceptable carrier. Such compositions can be used to administer the described isolated antibodies or antibody-binding fragments thereof to a subject or store or to maintain the described isolated antibodies or antibody-binding fragments thereof. Any of the described isolated antibodies or antibody-binding fragments thereof can be used to produce such compositions, which may include more than one of the disclosed isolated antibodies or antibody-binding fragments thereof. In addition, such compositions can include other agents, such as therapeutic agents, preservatives, antimicrobial agents, and the like.

Described herein are compositions comprising at least one disclosed antibody or an antigen-binding fragment thereof and a pharmaceutically acceptable carrier. The compositions can be formulated as any of various preparations that are known and suitable in the art, including those described and exemplified herein. In some embodiments, the compositions are aqueous formulations. Aqueous solutions can be prepared by admixing the antibodies or antigen-binding fragments thereof in water or suitable physiologic buffer, and optionally adding suitable colorants, flavors, preservatives, stabilizing and thickening agents and the like as desired. Aqueous suspensions can also be made by dispersing the antigen-binding fragments in water or physiologic buffer with viscous material, such as natural or synthetic gums, resins, methylcellulose, sodium carboxymethylcellulose, and other well-known suspending agents.

Also included are liquid formulations and solid form preparations which are intended to be converted, shortly before use, to liquid preparations. Such liquids include solutions, suspensions, syrups, slurries, and emulsions. Liquid preparations may be prepared by conventional means with pharmaceutically acceptable additives such as suspending agents (e.g., sorbitol syrup, cellulose derivatives or hydrogenated edible fats or oils); emulsifying agents (e.g., lecithin or acacia); non-aqueous vehicles (e.g., almond oil, oily esters, or fractionated vegetable oils); and preservatives (e.g., methyl or propyl-p-hydroxybenzoates or sorbic acid). These preparations may contain, in addition to the active agent, colorants, flavors, stabilizers, buffers, artificial and natural sweeteners, dispersants, thickeners, solubilizing agents, and the like. The compositions may be in powder or lyophilized form for constitution with a suitable vehicle such as sterile water, physiological buffer, saline solution, or alcohol, before use.

The compositions can be formulated for injection into a subject. For injection, the compositions described can be formulated in aqueous solutions such as water or alcohol, or in physiologically compatible buffers such as Hanks's solution, Ringer's solution, or physiological saline buffer. The solution may contain formulary agents such as suspending, stabilizing and/or dispersing agents. Injection formulations may also be prepared as solid form preparations which are intended to be converted, shortly before use, to liquid form preparations suitable for injection, for example, by constitution with a suitable vehicle, such as sterile water, saline solution, or alcohol, before use.

The compositions can be formulated in sustained release vehicles or depot preparations. Such long acting formulations may be administered by implantation (for example subcutaneously or intramuscularly) or by intramuscular injection. Thus, for example, the compositions may be formulated with suitable polymeric or hydrophobic materials (for example, as an emulsion in an acceptable oil) or ion exchange resins, or as sparingly soluble derivatives, for example, as a sparingly soluble salt. Liposomes and emulsions are well-known examples of delivery vehicles suitable for use as carriers for hydrophobic drugs.

The antibodies or fragments thereof described herein may be administered orally in any acceptable dosage form such as capsules, tablets, aqueous suspensions, solutions or the like. The proteins may also be administered parenterally including but not limited to: subcutaneous, intravenous, intramuscular, intra-articular, intra-synovial, intrasternal, intranasal, topically, intrathecal, intrahepatic, intralesional, and intracranial injection or infusion techniques. Generally, the antibodies and/or antigen-binding fragments thereof will be intravenously or intraperitoneally, for example, by injection.

Further disclosed herein are vectors encoding the isolated antibodies or antigen-binding fragments thereof described herein. A "vector" is a replicon, such as plasmid, phage, cosmid, or virus in which another nucleic acid segment may be operably inserted so as to bring about the replication or expression of the segment.

The term "operably linked" or "operably inserted" means that the regulatory sequences necessary for expression of the coding sequence are placed in a nucleic acid molecule in the appropriate positions relative to the coding sequence so as to enable expression of the coding sequence. By way of example, a promoter is operably linked with a coding sequence when the promoter is capable of controlling the transcription or expression of that coding sequence. Coding sequences can be operably linked to promoters or regulatory sequences in a sense or antisense orientation. The term "operably linked" is sometimes applied to the arrangement of other transcription control elements (e.g., enhancers) in an expression vector.

The terms "express" and "produce" are used synonymously herein, and refer to the biosynthesis of a gene product. These terms encompass the transcription of a gene into RNA. These terms also encompass translation of RNA into one or more polypeptides, and further encompass all naturally occurring post-transcriptional and post-translational modifications. The expression/production of an antibody or antigen-binding fragment can be within the cytoplasm of the cell, and/or into the extracellular milieu such as the growth medium of a cell culture.

Recombinant expression vectors contemplated to be within the scope of the description include synthetic, genomic, or cDNA-derived nucleic acid fragments that encode at least one recombinant protein which may be operably linked to suitable regulatory elements. Such regulatory elements may include a transcriptional promoter, sequences encoding suitable mRNA ribosomal binding sites, and sequences that control the termination of transcription and translation. Expression vectors, especially mammalian expression vectors, may also include one or more nontranscribed elements such as an origin of replication, a suitable promoter and enhancer linked to the gene to be expressed, other 5' or 3' flanking nontranscribed sequences, 5' or 3' nontranslated sequences (such as necessary ribosome binding sites), a polyadenylation site, splice donor and acceptor sites, or transcriptional termination sequences. An origin of replication that confers the ability to replicate in a host may also be incorporated. Such vectors may be integrated into the host genome or maintained independently in the cell or nucleus.

Further disclosed herein are recombinant cells expressing the isolated antibodies or antigen-binding fragments thereof described herein. The vectors described herein can be used to transform various cells with the genes encoding the disclosed antibodies or antigen-binding fragments thereof, and may be used to generate cells or cell lines producing the antibodies or antigen-binding fragment thereof. Thus, another aspect features host cells transformed with vectors comprising a nucleic acid sequence encoding the antibody or antigen-binding fragment thereof. The host cells disclosed herein can be prokaryotic or eukaryotic cells, for example the host cell can be a bacterium. In a preferred embodiment, the bacterial host cell can be $E.$ $coli$. Of course, the host cell can also be a mammalian cell, such as a Chinese hamster ovary (CHO) cell line. Numerous other such host cells, prokaryotic and eukaryotic, are known in the art and are considered to be within the scope of this disclosure. In some embodiments, the eukaryotic cells are a 293T cell or a Chinese Hamster Ovary (CHO) cell.

Cells transformed with the vectors described herein may be selected or screened for recombinant expression of the antibodies or antigen-binding fragments. Recombinant-positive cells are expanded and screened for subclones exhibiting a desired phenotype, such as high level expression, enhanced growth properties, or the ability to yield proteins with desired biochemical characteristics, for example, due to protein modification or altered post-translational modifications. These phenotypes may be due to inherent properties of a given subclone or to mutation. Mutations may be effected through the use of chemicals, UV-wavelength light, radiation, viruses, insertional mutagens, inhibition of DNA mismatch repair, or a combination of such methods.

Numerous techniques are known in the art for the introduction of foreign genes into cells and may be used to construct the recombinant cells. The technique used should provide for the stable transfer of the heterologous gene sequence to the host cell, such that the heterologous gene sequence is heritable and expressible by the cell progeny, and so that the necessary development and physiological functions of the recipient cells are not disrupted. Techniques which may be used include but are not limited to chromosome transfer (e.g., cell fusion, chromosome mediated gene transfer, micro cell mediated gene transfer), physical methods (e.g., transfection, spheroplast fusion, microinjection, electroporation, liposome carrier), viral vector transfer (e.g., recombinant DNA viruses, recombinant RNA viruses) and the like. Calcium phosphate precipitation and polyethylene glycol (PEG)-induced fusion of bacterial protoplasts with mammalian cells can also be used to transform cells.

It is fully contemplated that the vectors such as those described herein can be used to transform prokaryotic and/or eukaryotic cells to facilitate expression of the described isolated antibodies or antibody-binding fragments thereof. In some embodiments the described vectors are used to facilitate protein expression in bacteria, such as $E.$ $coli$. While any $E.$ $coli$ strain can be used to express the proteins described herein, some preferred strains include: BL21 (DE3), BL21-CodonPlus® (DE3)-RP, BL21-Codon Plus® (DE3)-RIL, BL21-(DE3)-pLysS (Stratagene). Eukaryotic cells can also be used with vectors to facilitate protein expression. While those of skill in the art will recognize that a wide variety of eukaryotic cells will be suitable for this purpose, some preferred embodiments include mammalian cells and insect cells. For example, in one embodiment Chinese hamster ovary (CHO) cells can be used with the vectors to facilitate expression of the antibody or antigen-binding fragment constructs provided herein. In alternative embodiments, insect cells, such as Sf9 cells or S2 cells, can be used to with the described vectors to facilitate expression of the antibody or antigen-binding fragment constructs provided herein. Furthermore, those of skill in the art will understand that vectors, not expressly disclosed herein, can be used for the same purpose of expressing, or replicating nucleic acids encoding, the described antibodies or antigen-binding fragments thereof.

The described isolated antibodies or antibody-binding fragments thereof can be encoded by a variety of polynucleotides capable of encoding the amino acid sequences provided herein. These polynucleotides can also be incorporated into vectors useful for the maintenance, replication, and/or expression of the polynucleotides encoding the disclosed antibodies or antigen-binding fragments thereof. The vectors described above can be used to engineer cells to express the antibodies or antigen-binding fragments thereof encoded by the polynucleotides disclosed herein.

Methods of Treatment

Also disclosed herein are methods of treating a subject having heparin-induced thrombocytopenia (HIT), the methods comprising administering to the subject a therapeutically effective amount of any of the disclosed isolated antibodies or antigen-binding fragments thereof so as to treat HIT. In some embodiments, administering to the subject a therapeutically effective amount of the isolated antibody or antigen-binding fragment treats HIT by reducing platelet factor 4 (PF4) oligomerization.

The subject can be any animal, and preferably is a mammal such as a human, mouse, rat, hamster, guinea pig, rabbit, cat, dog, monkey, donkey, cow, horse, pig, and the like. In some embodiments, the mammal is a human. In some embodiments, the mammal is other than a human. In some embodiments, the subject is a mammalian subject.

Also disclosed herein are methods for reducing the likelihood that a subject receiving the administration of heparin or a heparin-mimic will become afflicted with HIT, the method comprising administering to the subject a therapeutically effective amount of any of the disclosed isolated antibodies or antigen-binding fragments thereof. In some embodiments, administering to the subject a therapeutically effective amount of the isolated antibody or antigen-binding fragment reduces the likelihood that a subject receiving the administration of heparin or a heparin-mimic will become afflicted with HIT by reducing platelet factor 4 (PF4) oligomerization. In some embodiments, the isolated antibody or antigen-binding fragment thereof is administered before, after or concurrently with heparin. In some embodiments, the isolated antibody or antigen-binding fragment thereof is administered before heparin. In some embodiments, the isolated antibody or antigen-binding fragment thereof is administered after heparin. In some embodiments, the isolated antibody or antigen-binding fragment thereof is administered concurrently with heparin. In some embodiments, the heparin is a heparin fragment, low-molecular-weight heparin or unfractionated heparin.

In some embodiments, the isolated antibody or antigen-binding fragment thereof is administered before, after or concurrently with a heparin mimic. In some embodiments, the isolated antibody or antigen-binding fragment thereof is administered before a heparin mimic. In some embodiments, the isolated antibody or antigen-binding fragment thereof is administered after a heparin mimic. In some embodiments, the isolated antibody or antigen-binding fragment thereof is administered concurrently with a heparin mimic. In some embodiments, the heparin mimic is fondaparinux.

Also disclosed herein are uses of an effective amount of any of the disclosed isolated antibodies or antigen-binding fragments thereof in the treatment of heparin-induced thrombocytopenia (HIT).

Also disclosed herein are uses of any of the disclosed isolated antibodies or antigen-binding fragments thereof in the manufacture of a medicament for the treatment of heparin-induced thrombocytopenia (HIT).

EXAMPLES

The following examples are provided to further describe some of the embodiments disclosed herein. The examples are intended to illustrate, not to limit, the disclosed embodiments.

Example 1: Atomic Based Structural Engineering of the Humanized Antibody; Sequences/Mutations Based on the crystal structure of the PF4 monomer in complex with the Fab fragment of the murine anti-PF4 antibody RTO, a structure-based humanization strategy was applied for RTO. The human IgG4 Fc sequence was used to replace the mouse IgG2b Fc sequence to avoid the formation of immune complexes capable of activating Fcγ receptors. Murine sequences were used to change CDR regions into fully human sequence-derived V regions. Residues on or close to the interface between VL and VH domains and residues on the flanking regions of CDRs are critical and mutated back to murine sequences after structural modeling based on the crystal structure of the PF4/mRTOFab complex, including light chain Ser24, Arg39, Phe89, Gly102 and heavy chain Ala51, Asn76, Leu81 and Thr99 etc. N-glycosylation of heavy chain Asn118 in the PF4/mRTOFab complex crystal structure was observed, which is close to the heavy chain CDR3. Glycosylation sites close to CDRs may affect activity and future industrial manufacturing. Asparagine118 was successfully replaced with a Threonine in the humanized heavy chain constructs and it was found that the N118T mutation did not alter binding affinity.

Example 2: Expression/Purification of the huAbs and mAbs by 293T/CHO Cells; FPLC to Show Purity and Yield The heavy chain and light chain sequences were synthesized and cloned into pSectag vectors using the QuickChange® mutagenesis kit. Different combinations of heavy chain and light chain plasmids were then co-transfected into 293T cells or expi-CHO cells for expression. Antibodies secreted into the culture medium were concentrated and passed over a Protein A column followed by size exclusion chromatography using an AKTA-purifier FPLC system. The final yield was approximately 2 mg per liter culture media after transient expression in 293T cells and approximately 100 mg per liter after transient expression in expi-CHO cells (Table 1).

Example 3: Analysis of the Binding of Antibodies (huAbs and mAbs) Expressed in Mammalian Cells to PF4 Using Surface Plasmon Resonance The binding affinity of the mammalian-cell-expressed RTO antibodies to human PF4 immobilized on the surface of a CM5 chip was evaluated using Biacore technology. The humanized antibody (huLight, huHeavy) binds to human PF4 at nM levels (Table 1), which is almost identical to the hybridoma-expressed and mammalian-cell-expressed parental antibody mRTO (mLight, mHeavy).

TABLE 1

Yields and binding affinities of huRTO antibody to PF4 produced in different expression systems estimated by Biacore

| LightC | HeavyC | expression system | yield | Kd (nM) |
|---|---|---|---|---|
| mLight | mHeavy | hybridoma | high | 5 |
| mLight | mHeavy | 293T | 2 mg/L | 1 |
| mLight | huHeavy | 293T | 2 mg/L | 0.4 |
| huLight | huHeavy | 293T | 2 mg/L | 0.75 |
| huLight | huHeavy | expi-CHO | 100 mg/L | 2 |

Example 4: Binding of Humanized RTO to PF4 is Confirmed by ELISA

Figure 1:
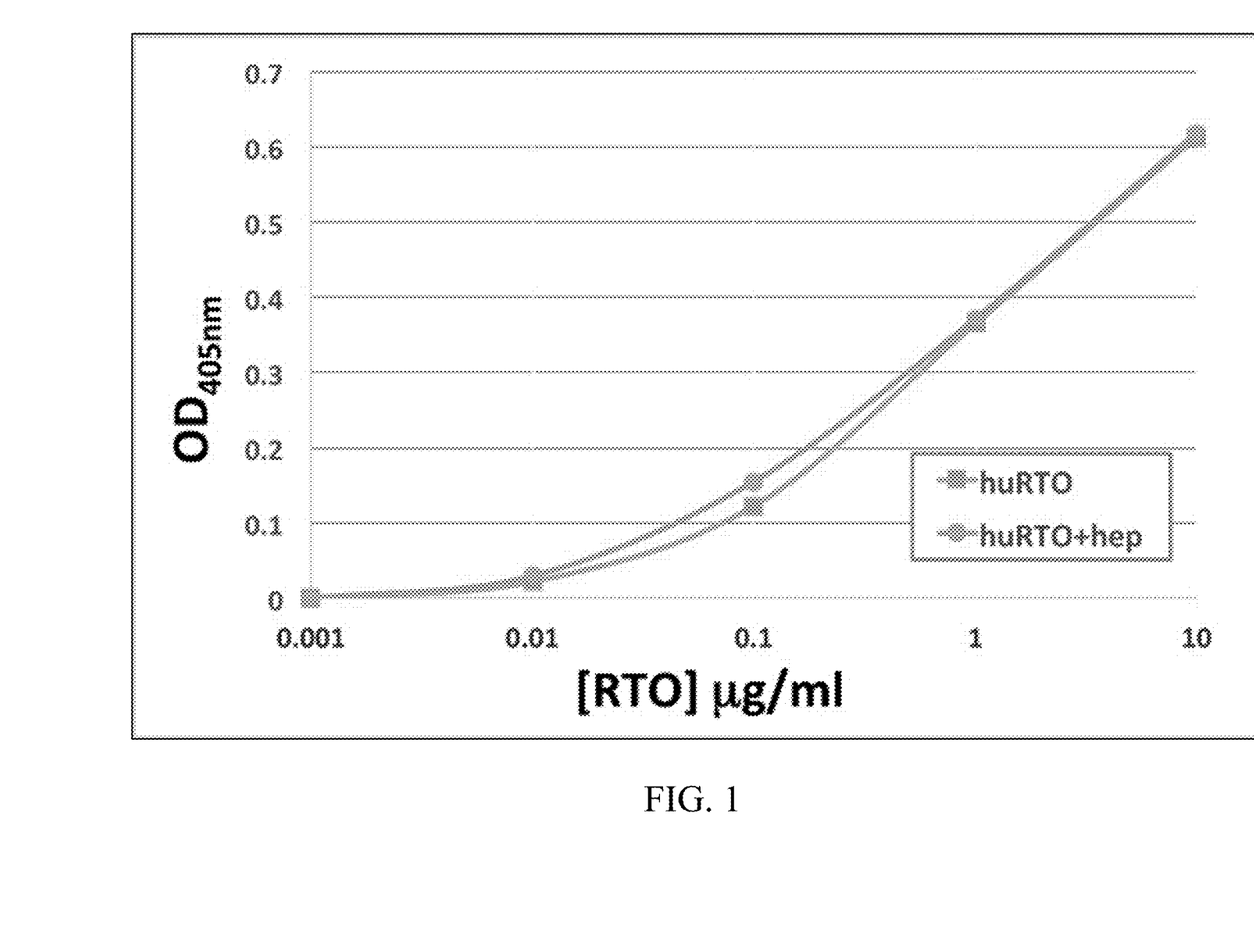

As depicted in FIG. 1, binding of huRTO (with human IgG4 Fc) to immobilized human PF4 was confirmed by ELISA test using goat anti-mouse and anti-human IgG Fc antibodies. Binding of huRTO to PF4 is independent of heparin.

Figure 2A:
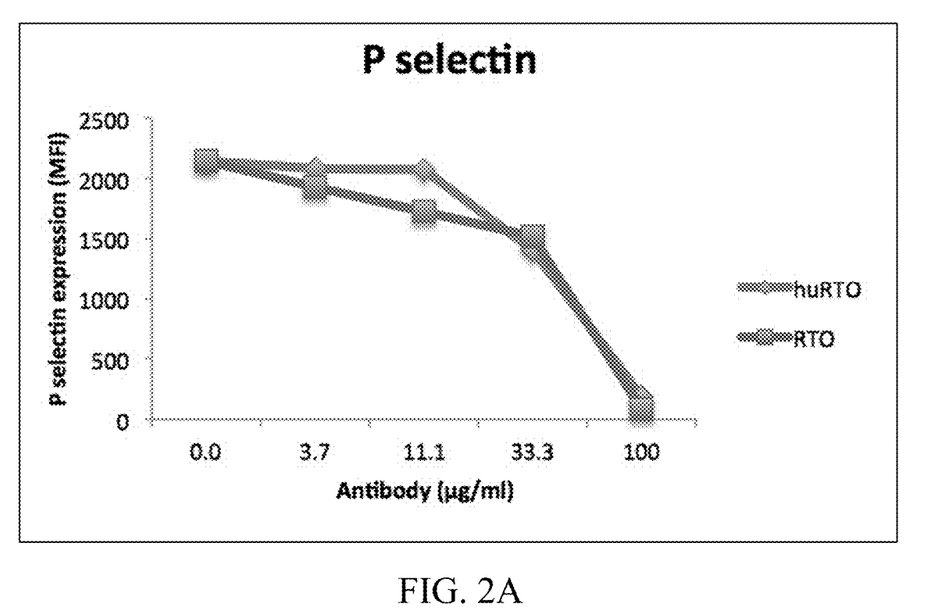
Figure 2B:
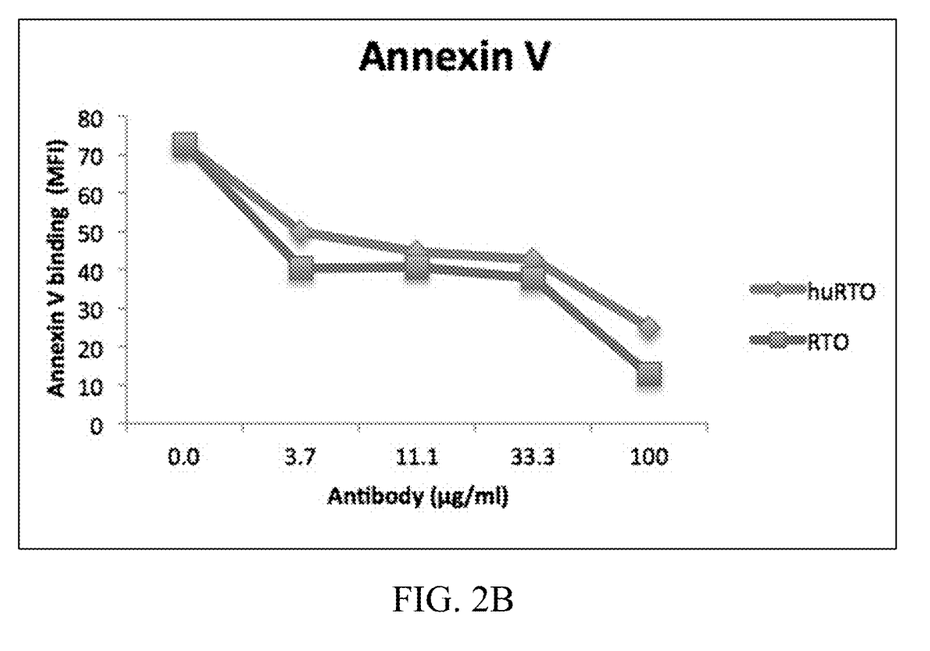

Example 5: HuRTO Inhibits Platelet Activation by a Pathogenic HIT Like Monoclonal Antibody KKO As depicted in FIG. 2A-FIG. 2B, mRTO or huRTO were added at indicated concentrations to PF4 before adding the whole blood. Samples were then stimulated with 10 μg/ml of the murine monoclonal antibody KKO for 30 min and platelet activation was monitored as mean fluorescence intensity of P selection expression or Annexin binding on platelets by flow cytometry.

Figure 3:
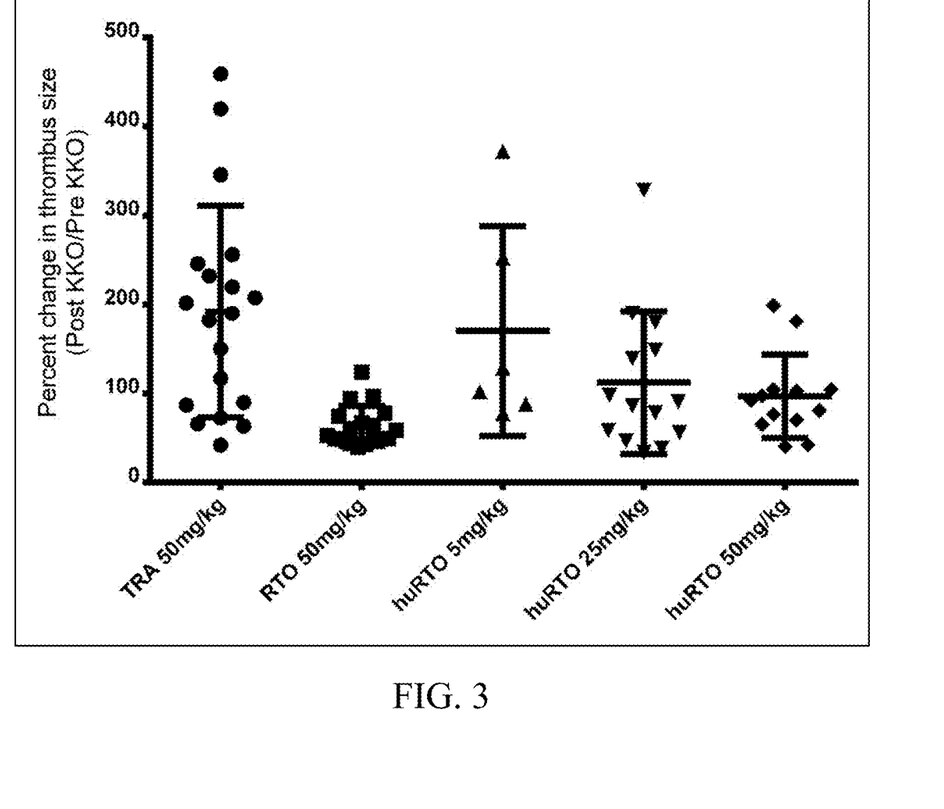

Example 6: HuRTO Prevents KKO-Induced Thrombosis Formation in a Laser Microvascular Injury Model As depicted in FIG. 3, the effect of huRTO on KKO induced thrombosis in a laser microvascular injury model. Antibodies (TRA, RTO and huRTO) were injected intravenously. Each dot denotes the percent change in thrombus size based on binding of fluorescently labelled platelets in mice receiving either huRTO, RTO or the TRA followed by KKO.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

The disclosures of each patent, patent application, and publication cited or described in this document are hereby incorporated herein by reference, in its entirety.

TABLE 2

Antibody segments of the described RTO antibodies and antigen-binding fragments thereof

| Antibody Segment | SEQ ID NO. | Sequence |
|---|---|---|
| Light chain CDR1 | 1 | SASQGINNYLS |
| Light chain CDR2 | 2 | YTSSLHS |
| Light chain CDR3 | 3 | QQFSKLPYT |
| Light chain CDR and framework region | 4 | SASQGINNYLSWYRQKPGKAPKLLIYYTSSLHSGVPSRFSGS GSGTDFTLTISSLQPEDFATYFCQQFSKLPYT |
| Light chain variable domain segment | 5 | DIQMTQSPSSLSASVGDRVTISCSASQGINNYLSWYRQKPGK APKLLIYYTSSLHSGVPSRFSGSGSGTDFTLTISSLQPEDFAT YFCQQFSKLPYTFGGGTKVEIK |
| Light chain | 6 | DIQMTQSPSSLSASVGDRVTISCSASQGINNYLSWYRQKPGK APKLLIYYTSSLHSGVPSRFSGSGSGTDFTLTISSLQPEDFAT YFCQQFSKLPYTFGGGTKVEIKRTVAAPSVFIFPPSDEQLKS GTASVVCLLNNFYPREAKVQWKVDNALQSGNSQESVTEQD SKDSTYSLSSTLTLSKADYEKHKVYACEVTHQGLSSPVTKS FNRGEC |
| Heavy chain CDR1 | 7 | GFAFSRYDMS |
| Heavy chain CDR2 | 8 | TITSGDNYTYYPDSVKG |
| Heavy chain CDR3 | 9 | QGLLYYAMDY |
| Heavy chain CDR and framework region | 10 | GFAFSRYDMSWVRQAPGKGLEWVATITSGDNYTYYPDSVK GRFTISRDNSKNTLYLQMNSLRAEDTAVYYCTRQGLLYYA MDY |
| Heavy chain variable domain segment | 11 | EVQLVESGGGLVQPGGSLRLSCAASGFAFSRYDMSWVRQA PGKGLEWVATITSGDNYTYYPDSVKGRFTISRDNSKNTLYL QMNSLRAEDTAVYYCTRQGLLYYAMDYWGQGTLVTVSS |
| Heavy chain | 12 | EVQLVESGGGLVQPGGSLRLSCAASGFAFSRYDMSWVRQA PGKGLEWVATITSGDNYTYYPDSVKGRFTISRDNSKNTLYL QMNSLRAEDTAVYYCTRQGLLYYAMDYWGQGTLVTVSSA STKGPSVFPLAPSSKSTSGGTAALGCLVKDYFPEPVTVSWNS GALTSGVHTFPAVLQSSGLYSLSSVVTVPSSSLGTQTYICNV NHKPSNTKVDKKVEPKYGPPCPSCPAPEFLGGPSVFLFPPKP KDTLMISRTPEVTCVVVDVSQEDPEVQFNWYVDGVEVHNA KTKPREEQFNSTYRVVSVLTVLHQDWLNGKEYKCKVSNKG LPSSIEKTISKAKGQPREPQVYTLPPSPEEMTKNQVSLTCLVK GFYPSDIAVEWESNGQPENNYKTTPPVLDSDGSFFLYSRLTV DKSRWQEGNVFSCSVMHEALHNHYTQKSLSLSLGK |

EMBODIMENTS

The following list of embodiments is intended to complement, rather than displace or superseded, the previous descriptions.

Embodiment 1. An isolated antibody, or antigen-binding fragment thereof, that immunospecifically binds to platelet factor 4 (PF4), the antibody or antigen-binding fragment thereof comprising a light chain CDR and framework region comprising SEQ ID NO: 4 and a heavy chain CDR and framework region comprising SEQ ID NO: 10.

Embodiment 2. The isolated antibody, or antigen-binding fragment thereof, of embodiment 1, wherein the isolated antibody or antigen-binding fragment thereof has a light chain variable domain comprising an amino acid sequence that is at least 95% identical to the amino acid sequence of SEQ ID NO: 5 and a heavy chain variable domain comprising an amino acid sequence that is at least 95% identical to the amino acid sequence of SEQ ID NO: 11, wherein the variability occurs outside of the CDRs.

Embodiment 3. The isolated antibody, or antigen-binding fragment thereof, of embodiment 1 or 2, wherein the isolated antibody or antigen-binding fragment thereof has a light chain variable domain comprising the amino acid sequence of SEQ ID NO: 5 and a heavy chain variable domain comprising the amino acid sequence of SEQ ID NO: 11.

Embodiment 4. The isolated antibody, or antigen-binding fragment thereof, of embodiment 3, wherein the light chain variable domain has the amino acid sequence of SEQ ID NO: 5 and the heavy chain variable domain has the amino acid sequence of SEQ ID NO: 11.

Embodiment 5. The isolated antibody, or antigen-binding fragment thereof, of any one of the preceding embodiments, wherein the isolated antibody or antigen-binding fragment thereof has a light chain comprising an amino acid sequence that is at least 95% identical to the amino acid sequence of SEQ ID NO: 6 and a heavy chain comprising an amino acid sequence that is at least 95% identical to the amino acid sequence of SEQ ID NO: 12, wherein the variability occurs outside of the CDRs.

Embodiment 6. The isolated antibody, or antigen-binding fragment thereof, of any one of the preceding embodiments, wherein the isolated antibody or antigen-binding fragment thereof has a light chain comprising the amino acid sequence of SEQ ID NO: 6 and a heavy chain comprising the amino acid sequence of SEQ ID NO: 12.

Embodiment 7. The isolated antibody, or antigen-binding fragment thereof, of embodiment 6, wherein the light chain has the amino acid sequence of SEQ ID NO: 6 and the heavy chain has the amino acid sequence of SEQ ID NO: 12.

Embodiment 8. The isolated antibody, or antigen-binding fragment thereof, of any one of the preceding embodiments, wherein the isolated antibody or antigen-binding fragment thereof is humanized.

Embodiment 9. The isolated antibody, or antigen-binding fragment thereof, of any one of the preceding embodiments, wherein the antibody isotype is IgG.

Embodiment 10. The isolated antibody, or antigen-binding fragment thereof, of any one of the preceding embodiments, wherein the antigen-binding fragment is a Fv, Fab, Fab', Fab'-SH or F(ab')2.

Embodiment 11. The isolated antibody, or antigen-binding fragment thereof, of any one of the preceding embodiments, wherein the antibody is a single chain antibody, a diabody, or a multispecific antibody formed from more than one antigen-binding fragment.

Embodiment 12. The isolated antibody, or antigen-binding fragment thereof, of any one of the preceding embodiments, wherein the isolated antibody or antigen-binding fragment thereof has an equilibrium dissociation constant ($K_D$) of less than about 5 nM with platelet factor 4 (PF4).

Embodiment 13. The isolated antibody, or antigen-binding fragment thereof, of any one of the preceding embodiments, which binds at least a portion of the same epitope to which RTO binds so as to reduce platelet factor 4 (PF4) oligomerization.

Embodiment 14. The isolated antibody, or antigen-binding fragment thereof, of any one of the preceding embodiments, wherein the epitope overlaps with a portion of the same epitope to which KKO binds.

Embodiment 15. The isolated antibody, or antigen-binding fragment thereof, of any one of the preceding embodiments, which binds to the same epitope as the epitope to which RTO binds.

Embodiment 16. The isolated antibody, or antigen-binding fragment thereof, of any one of the preceding embodiments, which reduces PF4 oligomerization.

Embodiment 17. isolated antibody, or antigen-binding fragment thereof, of embodiment 16, wherein the oligomerization is dimerization or tetramerization.

Embodiment 18. The isolated antibody, or antigen-binding fragment thereof, of any one of the preceding embodiments, which reduces the binding of KKO to PF4.

Embodiment 19. The isolated antibody, or antigen-binding fragment thereof, of any one of the preceding embodiments, which binds between the PF4 AB dimer interface.

Embodiment 20. A pharmaceutical composition comprising the isolated antibody or antibody fragment of any one of embodiments 1 to 19.

Embodiment 21. A vector encoding the isolated antibody or antigen-binding fragment thereof of any one of embodiments 1 to 19.

Embodiment 22. A recombinant cell expressing the isolated antibody, or antigen-binding fragment thereof, of any one of embodiments 1 to 19.

Embodiment 23. The recombinant cell of embodiment 22, wherein the recombinant cell is a eukaryotic cell, a yeast cell, a plant cell or a bacterium.

Embodiment 24. The recombinant cell of embodiment 23, wherein the eukaryotic cell is a 293T cell or a Chinese Hamster Ovary (CHO) cell.

Embodiment 25. A method of treating a subject having heparin-induced thrombocytopenia (HIT), the method comprising administering to the subject a therapeutically effective amount of the isolated antibody or antigen-binding fragment thereof of any one of embodiments 1 to 19 so as to treat HIT.

Embodiment 26. The method of embodiment 25, wherein administering to the subject a therapeutically effective amount of the isolated antibody or antigen-binding fragment thereof treats HIT by reducing platelet factor 4 (PF4) oligomerization.

Embodiment 27. A method for reducing the likelihood that a subject receiving the administration of heparin or a heparin-mimic will become afflicted with HIT comprising administering to the subject a therapeutically effective amount of the isolated antibody or antigen-binding fragment thereof of any one of embodiments 1 to 19.

Embodiment 28. The method of embodiment 27, wherein administering to the subject a therapeutically effective amount of the isolated antibody or antigen-binding fragment thereof reduces the likelihood that a subject receiving the administration of heparin or a heparin-mimic will become afflicted with HIT by reducing platelet factor 4 (PF4) oligomerization.

Embodiment 29. The method of embodiment 27 or 28, wherein the isolated antibody or antigen-binding fragment thereof is administered before, after or concurrently with heparin.

Embodiment 30. The method of embodiment 29, wherein the heparin is heparin fragment, low-molecular-weight heparin or unfractionated heparin.

Embodiment 31. The method of embodiment 27 or 28, wherein the isolated antibody or antigen-binding fragment thereof is administered before, after or concurrently with a heparin mimic.

Embodiment 32. The method of embodiment 31, wherein the heparin mimic is fondaparinux.

Embodiment 33. Use of an effective amount of the isolated antibody or antigen-binding fragment thereof of any one of embodiments 1 to 19 in the treatment of heparin-induced thrombocytopenia (HIT).

Embodiment 34. Use of the isolated antibody or antigen-binding fragment thereof of any one of embodiments 1 to 19 in the manufacture of a medicament for the treatment of heparin-induced thrombocytopenia (HIT).

What is claimed:

1. A polynucleotide encoding a light chain of an antibody, or antigen-binding fragment thereof, that immunospecifically binds to platelet factor 4 (PF4), wherein the light chain or antigen-binding fragment thereof comprises a light chain CDR and framework region comprising the amino acid sequence of SEQ ID NO: 4.

2. The polynucleotide of claim 1, wherein the light chain or antigen-binding fragment thereof comprises the amino acid sequence of SEQ ID NO: 6.

3. An expression vector comprising the polynucleotide of claim 2.

4. The polynucleotide of claim 1, wherein the light chain or antigen-binding fragment thereof comprises a light chain variable region comprising the amino acid sequence of SEQ ID NO: 5.

5. An expression vector comprising the polynucleotide of claim 4.

6. A host cell comprising the expression vector of claim 5.

7. The host cell of claim 6, wherein the host cell is a eukaryotic cell, a yeast cell, a plant cell or a bacterium.

8. The host cell of claim 7, wherein the eukaryotic cell is a 293T cell or a Chinese Hamster Ovary (CHO) cell.

9. An expression vector comprising the polynucleotide of claim 1.

10. A polynucleotide encoding a heavy chain of an antibody, or antigen-binding fragment thereof, that immunospecifically binds to platelet factor 4 (PF4), wherein the heavy chain or antigen-binding fragment thereof comprises a heavy chain CDR and framework region comprising the amino acid sequence of SEQ ID NO: 10.

11. The polynucleotide of claim 10, wherein the heavy chain or antigen-binding fragment thereof comprises the amino acid sequence of SEQ ID NO: 12.

12. An expression vector comprising the polynucleotide of claim 11.

13. The polynucleotide of claim 10, wherein the heavy chain or antigen-binding fragment thereof comprises a heavy chain variable region comprising the amino acid sequence of SEQ ID NO: 11.

14. An expression vector comprising the polynucleotide of claim 13.

15. A host cell comprising the expression vector of claim 14.

16. The host cell of claim 15, wherein the host cell is a eukaryotic cell, a yeast cell, a plant cell or a bacterium.

17. The host cell of claim 16, wherein the eukaryotic cell is a 293T cell or a Chinese Hamster ovary (CHO) cell.

18. An expression vector comprising the polynucleotide of claim 10.

* * * * *